US 8,480,556 B2

(12) United States Patent
Jacquetin (10) Patent No.: US 8,480,556 B2
(45) Date of Patent: *Jul. 9, 2013

(54) METHOD AND APPARATUS FOR TREATING PELVIC ORGAN PROLAPSES IN FEMALE PATIENTS

(75) Inventor: Bernard Jacquetin, Clermont-Ferrand (FR)

(73) Assignee: Ethicon, Inc., Somerville, NJ (US)

( * ) Notice: Subject to any disclaimer, the term of this patent is extended or adjusted under 35 U.S.C. 154(b) by 44 days.

This patent is subject to a terminal disclaimer.

(21) Appl. No.: 13/160,083

(22) Filed: Jun. 14, 2011

(65) Prior Publication Data

US 2011/0245591 A1    Oct. 6, 2011

Related U.S. Application Data

(63) Continuation of application No. 11/378,821, filed on Mar. 17, 2006, now Pat. No. 7,985,173, which is a continuation of application No. 10/377,260, filed on Feb. 28, 2003, now Pat. No. 7,131,944.

(60) Provisional application No. 60/361,503, filed on Mar. 1, 2002.

(51) Int. Cl.
*A61F 2/02* (2006.01)

(52) U.S. Cl.
USPC .............................. 600/30; 600/37

(58) Field of Classification Search
USPC .................. 600/29–32, 37; 128/DIG. 25, 885, 128/887; 606/151–158; 602/4–6
See application file for complete search history.

(56) References Cited

U.S. PATENT DOCUMENTS

| 3,182,662 A | 5/1965 | Shirodkar |
| 3,212,502 A | 10/1965 | Myers |
| 3,311,110 A | 3/1967 | Singeman |
| 3,372,696 A | 3/1968 | Beliveau et al. |
| 3,472,232 A | 10/1969 | Earl |
| 3,608,095 A | 9/1971 | Barry |
| 3,763,860 A | 10/1973 | Clarke |
| 3,858,783 A | 1/1975 | Kapitanov et al. |
| 3,924,633 A | 12/1975 | Cook et al. |
| 4,037,603 A | 7/1977 | Wendorff |
| 4,128,100 A | 12/1978 | Wendorff |
| 4,235,238 A | 11/1980 | Ogiu et al. |

(Continued)

FOREIGN PATENT DOCUMENTS

| AU | 278089 B | 6/1965 |
| AU | 441561 B | 1/1972 |

(Continued)

OTHER PUBLICATIONS

European Search Report for EP Application No. 11188151.2 dated Dec. 19, 2011.

(Continued)

*Primary Examiner* — John Lacyk (57) ABSTRACT

An anterior implant adapted to treat central and lateral cystoceles present in a female patient includes laterally extending stabilizing straps for supporting the implant between the patient's bladder and vagina independently of the patient's arcus tendineous fascia pelvis. Rectocele and hysterocele repairs can be carried out using a single posterior implant which, like the anterior implant, is provided with laterally extending stabilizing straps for supporting the implant between the patient's rectum and vagina.

4 Claims, 10 Drawing Sheets

U.S. PATENT DOCUMENTS

| | | |
|---|---|---|
| 4,392,495 A | 7/1983 | Bayers |
| 4,441,497 A | 4/1984 | Paudler |
| 4,509,516 A | 4/1985 | Richmond |
| 4,549,545 A | 10/1985 | Levy |
| 4,736,746 A | 4/1988 | Anderson |
| 4,930,674 A | 6/1990 | Barek |
| 4,946,467 A | 8/1990 | Ohi et al. |
| 5,013,292 A | 5/1991 | Lemay |
| 5,032,508 A | 7/1991 | Naughton et al. |
| 5,080,667 A | 1/1992 | Chen et al. |
| 5,112,344 A | 5/1992 | Petros |
| 5,180,385 A | 1/1993 | Sontag |
| 5,203,864 A | 4/1993 | Phillips |
| 5,250,033 A | 10/1993 | Evans et al. |
| 5,281,237 A | 1/1994 | Gimpelson |
| 5,290,297 A | 3/1994 | Phillips |
| 5,337,736 A | 8/1994 | Reddy |
| 5,361,782 A | 11/1994 | Bauer |
| 5,362,294 A | 11/1994 | Seitzinger |
| 5,368,595 A | 11/1994 | Lewis |
| 5,368,756 A | 11/1994 | Vogel et al. |
| 5,370,294 A | 12/1994 | Bauer |
| 5,382,257 A | 1/1995 | Lewis et al. |
| 5,383,904 A | 1/1995 | Totakura et al. |
| 5,403,328 A | 4/1995 | Shallmam |
| 5,441,508 A | 8/1995 | Gazielly et al. |
| 5,450,860 A | 9/1995 | O'Connor |
| 5,503,638 A | 4/1996 | Cooper et al. |
| 5,507,796 A | 4/1996 | Hasson |
| 5,520,700 A | 5/1996 | Beyar et al. |
| 5,540,240 A | 7/1996 | Bauer |
| 5,582,188 A | 12/1996 | Benderev et al. |
| 5,611,515 A | 3/1997 | Benderev et al. |
| 5,628,756 A | 5/1997 | Barker, Jr. et al. |
| 5,645,568 A | 7/1997 | Chervitz et al. |
| 5,741,299 A | 4/1998 | Rudt |
| 5,755,728 A | 5/1998 | Maki et al. |
| 5,807,403 A | 9/1998 | Beyar et al. |
| 5,816,258 A | 10/1998 | Jervis |
| 5,836,314 A | 11/1998 | Benderev et al. |
| 5,840,011 A | 11/1998 | Landgrebe et al. |
| 5,855,549 A | 1/1999 | Newman |
| 5,860,425 A | 1/1999 | Benderev et al. |
| 5,899,909 A | 5/1999 | Claren et al. |
| 5,899,999 A | 5/1999 | De Bonet |
| 5,934,283 A | 8/1999 | Willem et al. |
| 5,935,122 A | 8/1999 | Fourkas et al. |
| 5,972,000 A | 10/1999 | Beyar |
| 5,997,554 A | 12/1999 | Thompson |
| 6,010,447 A | 1/2000 | Kardjian |
| 6,030,393 A | 2/2000 | Corlew |
| 6,042,534 A | 3/2000 | Gellman et al. |
| 6,042,536 A | 3/2000 | Tihon et al. |
| 6,068,591 A | 5/2000 | Bruckner et al. |
| 6,110,101 A | 8/2000 | Tihon et al. |
| 6,117,067 A | 9/2000 | Gil-Vernet |
| 6,190,401 B1 | 2/2001 | Green et al. |
| 6,197,036 B1 | 3/2001 | Tripp et al. |
| 6,221,005 B1 | 4/2001 | Bruckner et al. |
| 6,273,852 B1 | 8/2001 | Lehe et al. |
| 6,306,079 B1 | 10/2001 | Trabucco |
| 6,334,446 B1 | 1/2002 | Beyar |
| 6,382,214 B1 | 5/2002 | Raz et al. |
| 6,406,423 B1 | 6/2002 | Scetbon |
| 6,475,139 B1 | 11/2002 | Miller |
| 6,478,727 B2 | 11/2002 | Scetbon |
| 6,491,703 B1 | 12/2002 | Ulmsten |
| 6,494,887 B1 | 12/2002 | Kaladelfos |
| 6,575,897 B1 | 6/2003 | Ory et al. |
| 6,575,984 B2 | 6/2003 | Beyar |
| 6,575,998 B2 | 6/2003 | Beyar |
| 6,592,610 B2 | 7/2003 | Beyar |
| 6,595,911 B2 | 7/2003 | LoVuolo |
| 6,605,097 B1 | 8/2003 | Lehe et al. |
| 6,612,977 B2 | 9/2003 | Staskin et al. |
| 6,652,450 B2 | 11/2003 | Neisz et al. |
| 6,691,711 B2 | 2/2004 | Raz et al. |
| 6,692,506 B1 | 2/2004 | Ory et al. |
| 6,802,807 B2 | 10/2004 | Anderson et al. |
| 6,808,486 B1 | 10/2004 | O'Donnell |
| 6,808,487 B2 | 10/2004 | Migliari |
| 6,830,052 B2 | 12/2004 | Carter et al. |
| 7,131,944 B2 | 11/2006 | Jacquetin |
| 7,985,173 B2 | 7/2011 | Jacquetin |
| 2001/0018549 A1 | 8/2001 | Scetbon |
| 2001/0049467 A1 | 12/2001 | Lehe et al. |
| 2002/0028980 A1 | 3/2002 | Thierfelder et al. |
| 2002/0058959 A1 | 5/2002 | Gellman |
| 2002/0077526 A1 | 6/2002 | Kammerer et al. |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0107430 A1 | 8/2002 | Neisz et al. |
| 2002/0147382 A1 | 10/2002 | Neisz et al. |
| 2002/0151762 A1 | 10/2002 | Rocheleau et al. |
| 2002/0161382 A1 | 10/2002 | Neisz et al. |
| 2002/0188169 A1 | 12/2002 | Kammerer et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0050530 A1 | 3/2003 | Neisz et al. |
| 2003/0062052 A1 | 4/2003 | Carter et al. |
| 2003/0078468 A1 | 4/2003 | Skiba et al. |
| 2003/0149440 A1 | 8/2003 | Kammerer et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0191360 A1 | 10/2003 | Browning |
| 2003/0195386 A1 | 10/2003 | Thierfelder et al. |
| 2003/0212305 A1 | 11/2003 | Anderson et al. |
| 2003/0220538 A1 | 11/2003 | Jacquetin |
| 2004/0015048 A1 | 1/2004 | Neisz et al. |
| 2004/0039453 A1 | 2/2004 | Anderson et al. |
| 2004/0068159 A1 | 4/2004 | Neisz et al. |
| 2004/0106845 A1 | 6/2004 | Anderson et al. |
| 2004/0225181 A1 | 11/2004 | Chu et al. |
| 2004/0243166 A1 | 12/2004 | Odermatt et al. |
| 2004/0249240 A1 | 12/2004 | Goldmann et al. |
| 2004/0249397 A1 | 12/2004 | Delorme et al. |
| 2006/0134159 A1 | 6/2006 | Nicita |
| 2011/0245590 A1* | 10/2011 | Jacquetin .................. 600/30 |

FOREIGN PATENT DOCUMENTS

| | | |
|---|---|---|
| CA | 2428652 A1 | 5/2002 |
| DE | 4334419 A1 | 4/1995 |
| DE | 19544162 C1 | 4/1997 |
| EP | 0598976 B1 | 6/1994 |
| EP | 0774240 B1 | 5/1997 |
| EP | 0941712 A1 | 9/1999 |
| EP | 1025811 A2 | 8/2000 |
| SE | 503271 C2 | 4/1996 |
| WO | WO 90/03766 A1 | 4/1990 |
| WO | WO 96/06567 A1 | 3/1996 |
| WO | WO 97/13465 A1 | 4/1997 |
| WO | WO 98/31301 A1 | 7/1998 |
| WO | WO 00/27304 A1 | 5/2000 |
| WO | WO 01/06951 A1 | 2/2001 |
| WO | WO 02/38079 A2 | 5/2002 |
| WO | WO 03/073960 A1 | 9/2003 |
| WO | WO 2004/012626 A1 | 2/2004 |

OTHER PUBLICATIONS

Giberti, Claudio, "Transvaginal Sacrospinous Colpoplexy by Palpation—A New Minimally Invasive Procedure Using An Anchoring System," Urology, 57(4), 666-668 (2001), Elsevier Science Inc., Ospedale San Paolo, Italy.

Leanza, V. et al., "New Technique for Correcting Both Incontinence and Cystocele T.I.C.T. (Tension-Free Incontinence Cystocele Treatment)". Urogynaecologia International Journal, 2001, No. 3515, pp. 133-140.

Collinet, P., et al., "The Vaginal Patch for Vaginal Cure of Cystocele", J. Gynecol. Obstet, Biol. Reprod./vol. 29, No. 2, 2000, pp. 197-201.

Cosson, M. et al., "Cystocele Repair by Vaginal Patch Short-Term Results in 47 Patients", Progres en Urologie. 2001. 11. pp. 340-346.

Petros, P.E., Papa, "Vault Prolapse I: Dynamic Supports of the Vagina", International Urogynecol Journal (2001). vol. 12, pp. 292-295, Springer-Verlag London Ltd.

Petros, P.E. Papa, "Vault Prolapse II: Restoration of Dynamic Vaginal Supports by Infracoccygeal Sacropexy, an Axial Day-Case Vaginal Procedure". International Urogynecol Journal (2001) vol. 12, pp. 296-303, Springer-Verlag London Ltd.

"AMS Sparc (TM) Sling System", American Medical Systems, Inc., Minnetonka, MN, 2001, pp. 1-7.

"TVT Tension-Free Vaginal Tape—Innovative Surgical Alternative for the Treatment of Female Stress Urinary Incontinence", Gynecare, Ethicon, Inc., 1999, pp. 1-6.

Second Office Action issued on Nov. 21, 2008, in connection with Applicat's corresponding Chinese Patent Application No. 03807622.5.

Third Office Action issued on Apr. 3, 2009, in connection with Applicat's corresponding Chinese Patent Application No. 03807622.5.

Communication Pursuant to Article 94(3) EPC issued on Nov. 9, 2009, in connection with Applicat's corresponding European Patent Application No. 03743476.8.

Communication Pursuant to Article 94(3) EPC issued on Aug. 8, 2011, in connection with Applicat's corresponging European Patent Application No. 03743476.8.

Official Action issued on Jun. 10, 2008 in connection with Applicat's corresponding Japanese Patent Application No. 2003-572485.

Notice of Grounds for Rejection issued on Dec. 28, 2007 in connection with Applicat's corresponding Korean Patent Application No. 2004-7013616.

Official Action issued on Nov. 3, 2006 in connection with Applicat's corresponding Norwegian Patent Application No. 20043785 with English translation.

Official Action issued on May 15, 2007 in connection with Applicat's corresponding Norwegian Patent Application No. 20043785 with English translation.

Official Action issued on Aug. 21, 2007 in connection with Applicat's corresponding Norwegian Patent Application No. 20043785 with English translation.

Office Action issued on Jan. 25, 2007 in connection with Applicat's corresponding Canadian Patent Application No. 2,477,834.

Notice of Grounds for Rejection issued on Nov. 9, 2005 in connection with Applicant's corresponding Korean Patent Application No. 2004-7013616 with English translation.

Notice of Final Rejection issued on Jul. 23, 2007 in connection with Applicat's corresponding Korean Patent Application No. 2004-7013616 with English translation.

Examiner's First Report issued on Jul. 11, 2007 in connection with Applicat's corresponding Australian Patent Application No. 2003315843.

PCT International Search Report issue on Aug. 18, 2003 in connection with Applicat's corresponding International Patent Application No. PCT/IB03/01231.

PCT Written Opinion issued on Dec. 29, 2003 in connection with Applicat's corresponding International Patent Application No. PCT/IB03/01231.

PCT International Preliminary Examination Report issued on Apr. 23, 2004 in connection with Applicat's corresponding International Patent Application No. PCT/IB03/01231.

Pre-Interview Office Action mailed on Jun. 25, 2010 in connection with Applicat's corresponding U.S. Appl. No. 11/378,821, which is a patent of the present application.

First Action Interview mailed on Jan. 4, 2011 in connection with Applicat's corresponding U.S. Appl. No. 11/378,821, which is a parent of the present application.

Office Action mailed on Feb. 8, 2005 in connection with Applicat's corresponding U.S. Appl. No. 10/377,260, which is a parent of the present application.

Final Office Action mailed on Sep. 9, 2005 in connection with Applicat's corresponding U.S. Appl. No. 10/377,260, which is a parent of the present application.

* cited by examiner

METHOD AND APPARATUS FOR TREATING PELVIC ORGAN PROLAPSES IN FEMALE PATIENTS

CROSS REFERENCE TO RELATED APPLICATIONS

This application is a continuation of U.S. patent application Ser. No. 11/378,821, filed Mar. 17, 2006 now U.S. Pat. No. 7,985,173, which is a continuation of U.S. patent application Ser. No. 10/377,260, filed Feb. 28, 2003 now U.S. Pat. No. 7,131,944, which claims the benefit of U.S. Provisional Patent Application Ser. No. 60/361,503, filed Mar. 1, 2002. All of the foregoing related patent applications are incorporated by reference herein in their entirety.

FIELD OF THE INVENTION

The present invention relates to surgical devices and procedures useful for treating pelvic organ prolapses in female patients.

BACKGROUND OF THE INVENTION

Women, often due to age, can experience three basic types of pelvic organ prolapses. These prolapses or defects are as follows: cystocele; hysterically; and rectocele.

A cystocele occurs when the bladder bulges into the vagina. If the defect, is confined to a centralized region, it is commonly referred to as a central cystocele. If the defect extends laterally beyond any such centralized region, the laterally extending portion(s) is commonly referred to as a lateral cystocele(s). Cystoceles, in general, are treated by an anterior repair which, in the past, has involved a suturing procedure or the use of an implant adapted to support the bladder in a hammock-like fashion (see, for instance, U.S. Pat. No. 5,840,011 and WIPO Publication No. WO 02/38079 A2). The known suturing procedures suffer from a high reoccurrence rate. The aforementioned implants, while having proved successful for the treatment of a central cystocele, are not inherently designed to treat a lateral cystocele(s).

A rectocele occurs when the rectum bulges into the vagina. This type of defect is treated by a posterior repair which, in the past, has involved suspension of the vaginal apex to the cardinal and uterosacral ligaments. Variations of these procedures have been performed using various mesh materials.

A hysterocele occurs when the uterus descends into the vagina, resulting in a vaginal vault descent. The common treatment for such a defect is a hysterectomy, followed with a vaginal vault suspension carried out by, for instance, attaching the resulting vaginal cuff to the levator ani, to the cocuygenous muscle, or to one of the sacrospinous ligaments, but not to both of them (the Richter technique).

SUMMARY OF THE INVENTION

One aspect of the present invention involves a new and improved anterior implant and a procedure for using it to make cystocele repairs in a female patient. More particularly, the anterior implant includes an inboard area adapted to treat a lateral cystocele and a pair of flanking outboard areas, each of which is adapted to treat a lateral cystocele. After positioning the body of the anterior implant between the patient's bladder and vagina, laterally extending straps are passed through the patient's obturator foreamens and corresponding skin incisions in the patient's perineum. The straps function to stabilize the anterior implant on both sides thereof independently of the patient's arcus tendineous fascia pelvis. In one embodiment, the anterior implant is provided with a pair of stabilizing straps, one on each side of the implant. In another embodiment, two pairs of stabilizing straps are provided, one pair extending laterally from one side of the anterior implant and another pair extending laterally from the opposite side of the anterior implant.

Another aspect of the present invention involves a new and improved posterior implant and a procedure for using it to treat a rectocele and/or a hysterocele present in a female patient. The posterior implant includes laterally extending straps for supporting the body of the posterior implant between the rectum and the vagina, while also functioning to perform a vaginal vault suspension through their attachment to the sacrospinous ligaments.

BRIEF DESCRIPTION OF THE DRAWINGS

For a better understanding of the present invention, reference is made to the following detailed description of various exemplary embodiments considered in conjunction with the accompanying drawings, in which.

DETAILED DESCRIPTION OF THE EXEMPLARY EMBODIMENTS

Figure 1:
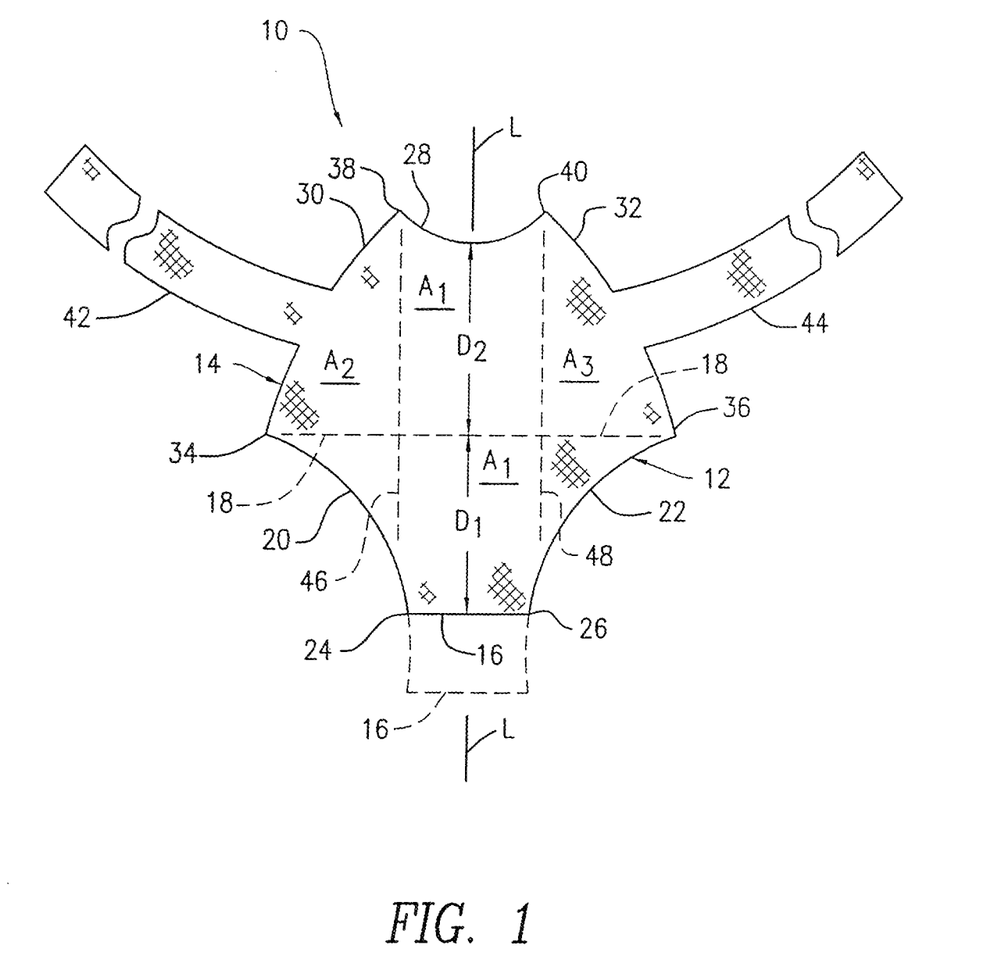
FIG. 1 is a top plan view of one exemplary embodiment of an anterior implant constructed in accordance with the present invention.

With reference to FIG. 1, an anterior implant 10 includes a lower portion 12 and an upper portion 14. While two distinct portions have been identified, it should be understood that the anterior implant 10 is preferably made from a single sheet of any suitable bio-compatible mesh material, such as a knitted polypropylene fabric (e.g., soft PROLENE® mesh marketed by Ethicon, Inc. of Somerville, N.J.; U.S.A.). Accordingly, the imaginary boundaries of the various portions are indicated in FIG. 1 by dotted lines (i.e., in phantom) to facilitate consideration and discussion of the anterior implant 10.

Returning now to FIG. 1, the lower portion 12, which has a generally funnel-like shape, is demarcated by a straight lower edge 16 having a length in a range of from about 2 cm to about 5 cm, an imaginary border 18 (indicated in phantom in FIG. 1) having a length in a range of from about 8 cm to about 14 cm, and a pair of concave side edges 20, 22 having a complex (i.e., compound) arcuate shape approximating that of a female patient's pelvic anatomy. Corners 24, 26 are formed where the lower edge 16 merges with the concave side edges 20, 22, respectively. It should be noted that the lower edge 16 can be extended by as much as about 3 cm (as indicated in phantom in FIG. 1) for a purpose to be described hereinafter.

The distance $D_1$ between the lower edge 16 and the imaginary border 18 is also selected as a function of the pelvic anatomy of the patient, but typically falls within a range of from about 4 cm to about 8 cm. Of course, the nature of the mesh fabric from which the anterior implant 10 is made is such that the surgeon can modify the size and shape of the lower portion 12 to meet the needs of a particular patient. In other words, the lower portion 12 of the anterior implant 10 can be custom fitted in the surgical arena.

Still referring to FIG. 1, the upper portion 14, which has a generally dome-like shape, is demarcated by the imaginary border 18 with the lower portion 12, a curved upper edge. 28 having a radius (e.g., from about 2 cm to about 4 cm) and arcuate length (e.g., from about 2 cm to about 4 cm) selected so as to avoid contact with the bladder neck of the patient, and a pair of convex side edges 30, 32 having a complex arcuate shape approximating that of the arcus tendineous fascia pelvic (ATFP). The convex side edges 30, 32 of the upper portion 14 merge with the concave side edges 20, 22, respectively, of the lower portion 12 to form corners 34, 36, respectively, while corners 38, 40 are formed where the upper edge 28 merges with the convex side edges 30, 32, respectively.

The distance $D_2$, as measured along the central longitudinal axis (L) of the anterior implant 10 and between the imaginary border 18 and the upper edge 28, is selected as a function of the pelvic anatomy of the patient. Typically, the distance $D_2$ falls within a range of from about 3 cm to about 5 cm. Like the lower portion 12, the upper portion 14 is adapted for custom fitting in the surgical arena to meet the particular needs of a patient. Thus, it should be understood that the shape and size of the upper portion 14 are subject to post-manufacture modification by the surgeon during the course of a surgical procedure.

With continuing reference to FIG. 1, straps 42, 44 extend outwardly from opposite sides of the upper portion 14. More particularly, the strap 42 extends laterally outward from the convex side edge 30 of the upper portion 14, while the strap 44 extends laterally outward from the convex side edge 32 of the upper portion 14. The straps 42, 44, whose function will be described in detail hereinafter, typically have a width in a range of from about 0.5 cm to about 2 cm, and a length in a range of from about 7 cm to about 15 cm. While the straps 42, 44 preferably have a slight curvature as shown in FIG. 1, they could also extend in a linear fashion from the convex sides edges 30, 32, respectively, of the anterior implant 10. As explained previously, the surgeon can readily modify the width and length of the straps 42, 44 by, for instance, cutting them with scissors or other suitable cutting instruments. Straps 42, 44 are preferably formed monolithically with the upper portion 14.

Imaginary boundary lines 46, 48, which extend generally parallel to the central longitudinal axis (L), divide the body of the anterior implant 10 into an inboard area $A_1$ and two outboard areas $A_2$, $A_3$ which flank the inboard area $A_1$. The areas $A_1$, $A_2$, and $A_3$ are not precise. Generally speaking, the area $A_1$ designates that portion of the anterior implant 10 which would function to repair a central or medial cystocele in accordance with a surgical procedure to be described in detail hereinafter, while the areas $A_2$, $A_3$ designate those portions of the anterior implant 10 which would function to repair lateral cystoceles in accordance with the same procedure.

Figure 2:
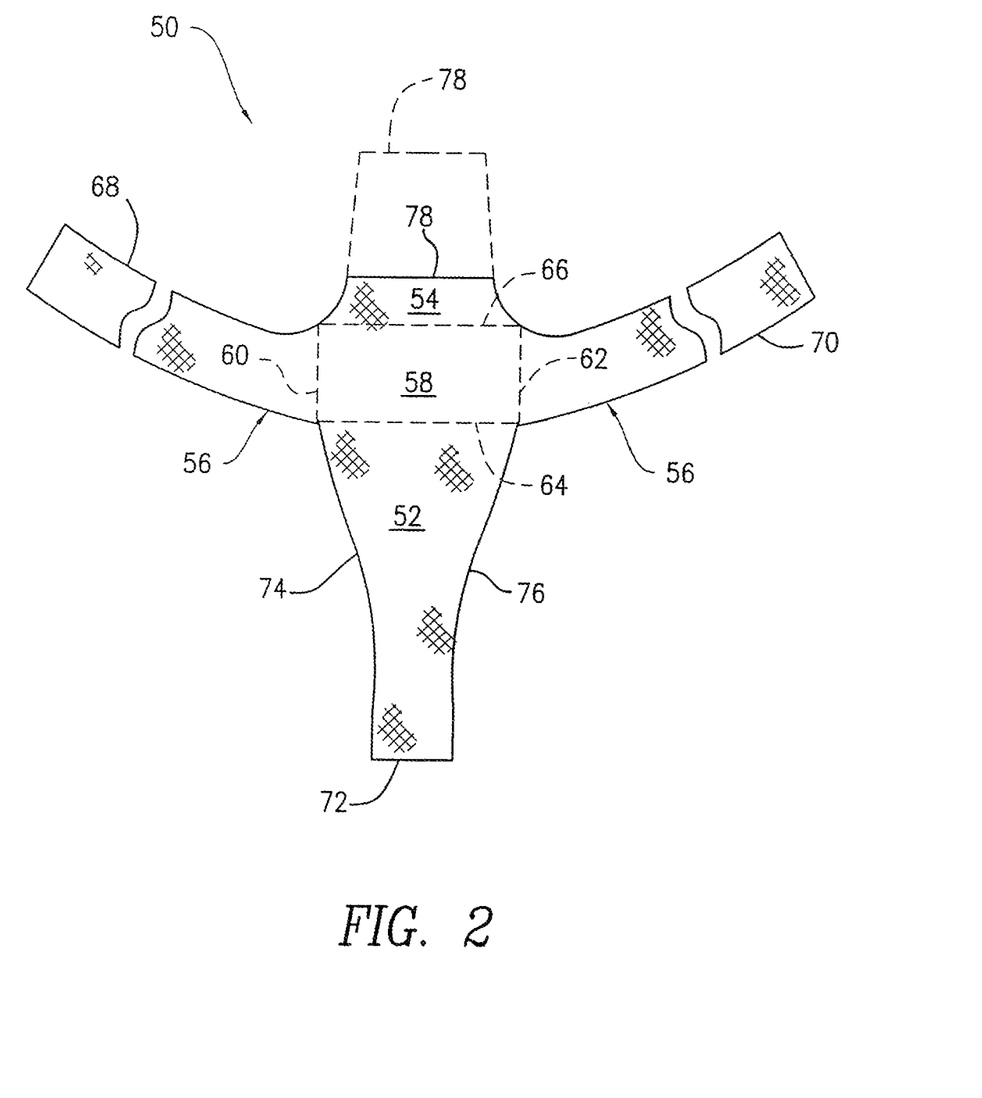
FIG. 2 is a top plan view of one exemplary embodiment of a posterior implant constructed in accordance with the present invention.

With reference now to FIG. 2, a posterior implant 50 includes a lower portion 52, an upper portion 54, and a tape portion 56. Like the anterior implant 10, the posterior implant 50 is made from a single sheet of any suitable biocompatible mesh material. Although the posterior implant 50 is depicted in FIG. 2 as being separate and distinct from the anterior implant 10, it should be understood that the posterior implant 50 can be formed integrally (i.e., monolithically) with the anterior implant 10 as will be described in greater detail hereinafter. As was the case when describing the anterior implant 10 of FIG. 1, the imaginary boundaries of the various portions of the posterior implant 50 of FIG. 2 are indicated by dotted lines (i.e., in phantom) to facilitate consideration and discussion.

Returning now to FIG. 2, the tape portion 56, which is interposed between the lower portion 52 and the upper portion 54, has an imaginary central region 58 bounded by imaginary lines 60, 62, 64 and 66 and approximating the shape of a rectangle having a length of about 5 cm and a width of about 0.5 to 2 cm. The tape portion 56 also includes a pair of straps 68, 70 extending outwardly from opposite ends of the imaginary central region 58. The straps 68, 70, whose function will be described in greater detail hereinafter, typically have a width in a range of from about 0.5 cm to about 2 cm, a length of about 4 cm, if the straps 68, 70 are attached to and terminated at the sacrospinous ligaments, or about 20 cm, if the straps 68, 70 are passed through the pelvic floor via the buttocks with or without passing through the sacrospinous ligaments. While the straps 68, 70 preferably have a slight curvature as shown in FIG. 2, they could also extend in a linear fashion from opposite sides of posterior implant 50. Given the nature of the mesh material from which the posterior implant 50 is made, the width and length of the straps 68, 70 can be readily modified by the surgeon to meet the needs of a particular patient.

Still referring to FIG. 2, the lower portion 52, which has a generally triangular shape, depends downwardly from the tape portion 56. More particularly, the lower portion 52 is demarcated by a straight lower edge 72 having a length in a range of from about 1.5 cm to about 3.5 cm and a pair of downwardly converging side edges 74, 76 which are either straight or slightly concave. While the length of the side edges 74, 76 is typically in a range of from about 8 cm to about 12 cm, it should be appreciated by a person skilled in the art that the physical dimensions of the lower portion 52, including the length of the side edges 74, 76, are a function of the pelvic anatomy of the patient. More particularly, the size and shape of the lower portion 52 are specifically selected for the purpose of repairing a rectocele. A person skilled in the art will also appreciate that the shape and size of the lower portion 52 are subject to post-manufacture modification by the surgeon. In cases where a rectocele repair is not required but a vaginal vault suspension is, both the lower portion 52 and the upper portion 54 can be removed from the posterior implant 50, leaving the tape portion 56 to perform the vaginal vault suspension.

With continuing reference to FIG. 2, the upper portion 54, which is demarcated at its free end by an upper edge 78 and which otherwise approximates the shape of a rectangle having a length of from about 3 cm and a width of about 1 cm, extends upwardly from the tape portion 56. The primary purpose of the upper portion 54 is to provide a means for attaching the posterior implant 50 to the anterior implant 10. Thus, for a patient who does not need the anterior implant 10, it should be appreciated that the upper portion 54 of the posterior implant 50 can be removed by the surgeon before insertion of the posterior implant 50 in such patient. It should also be appreciated that the surgeon can otherwise modify the size and shape of the upper portion 54 to meet his or her needs, such as when attaching the posterior implant 50 to the anterior implant 10. For instance, the upper edge 78 can be extended by as much as about 3 cm (as indicated in phantom in FIG. 2) to facilitate attachment of the posterior implant 50 to the anterior implant 10. For instance, the upper edge 78 can be extended by as much as about 3 cm (as indicated in phantom in FIG. 2) to facilitate attachment of the posterior implant to the anterior implant 10. Alternatively, such attachment can be facilitated by extending the lower edge 16 of the anterior implant 10 as described herein.

Both the anterior implant 10 and the posterior implant 50 can be cut or punched out from a larger piece of the mesh fabrics mentioned hereinabove. If necessary, the loose ends of the severed filaments can be treated against unraveling by any suitable technique known in the art.

The anterior implant 10 and the posterior implant 50 may be provided in a variety of standard shapes and sizes (e.g., small, medium and large). After comparing these standard implants to the pelvic anatomy of a particular patient, the surgeon would select the one which best meets the patient's needs. If any modifications to the size and/or shape of the selected implant are required, they can be effected by the surgeon in the surgical arena.

The anterior implant 10 is used to make an anterior repair of a cystocele, while the posterior implant 50 is used to make a posterior repair of a rectocele. A vaginal vault suspension can be performed using the anterior implant 10 and/or the posterior implant 50. All of these treatments will be discussed in greater detail below.

I. Overview

A standard vaginal hysterectomy usually precedes any pelvic floor repair carried out in accordance with the present invention. Thus, as shown in FIG. 3, a vagina (V) is illustrated without its associated uterus.

Figure 3:
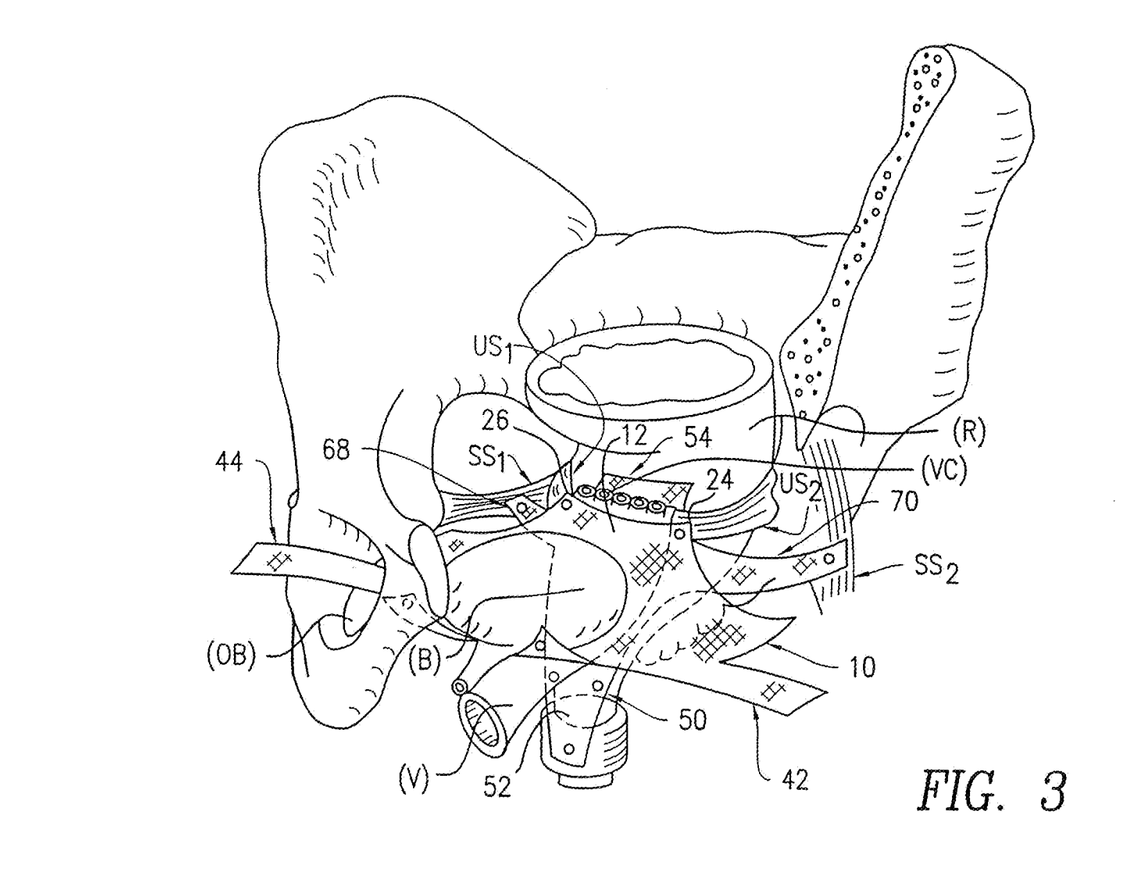
FIG. 3 is an illustration of a female's pelvic anatomy which has undergone surgical procedures using the implants of FIGS. 1 and 2.

Referring still to FIG. 3, a cystocele has been treated by an anterior repair performed with the anterior implant 10 of FIG. 1. Briefly, such a treatment involves the placement of the anterior implant 10 between the vagina (V) and the bladder (B).

FIG. 3 also illustrates how a rectocele has been treated by a posterior repair performed with the posterior implant 50 of FIG. 2. Briefly, such a treatment involves the placement of the posterior implant 50 between the vagina (V) and the rectum (R).

Since the uterus (not shown) has been removed from the vagina (V), an apical repair is also illustrated in FIG. 3. Briefly, such a repair involves using the anterior implant 10 and/or the posterior implant 50 to perform a vaginal vault suspension.

II. Anterior and Lateral Repair

A. Incision of the Anterior Vaginal Wall

The full thickness of the anterior vaginal wall is incised longitudinally to create an appropriately sized anterior vaginal incision. If respecting the bladder neck area and the apical part of the vagina, the anterior median colpotomy would start 3 cm from the vaginal vault and would stop at least 1 cm from the bladder neck. If respecting the bladder neck area only, the anterior median colpotomy would start at the vaginal vault and would stop at least 1 cm from the bladder neck. Although not illustrated in the accompanying drawings, these procedures are well known to a person skilled in the art.

B. Bladder Dissection

This well known procedure, which is not illustrated in the accompanying drawings, involves a lateral dissection up to the vaginal cul-de-sac. The integrity of the endopelvic fascia is then checked.

In the absence of a defect, the dissection is carried out following the plane of the fascia until the inferior edge of the pubic ramus is reached. After inserting scissors between the levator ani and the bone, a finger is passed through the opening and then pushed until it comes into contact with the obturator membrane. Such a procedure is commonly referred to as a supra levator passage.

If, on the other hand, a lateral defect or a very weak fascia is found, the paravesical fossa is first opened with a finger. Since a complete dissection of the arcus tendinosus fascia pelvis is unnecessary, the finger feels the obturator foramen through the muscular pelvic side wall (levator ani and obturator muscles). Such a procedure is commonly referred to as a trans-levator passage.

C. Plication of the Pre-Vesical Fascia

This procedure is typically performed using a continuous suture of 2/0 absorbable monofilament suture. While not illustrated in the accompanying drawings, the procedure is well known to a person skilled in the art.

D. Trans-Obturator Passage

Figure 4:
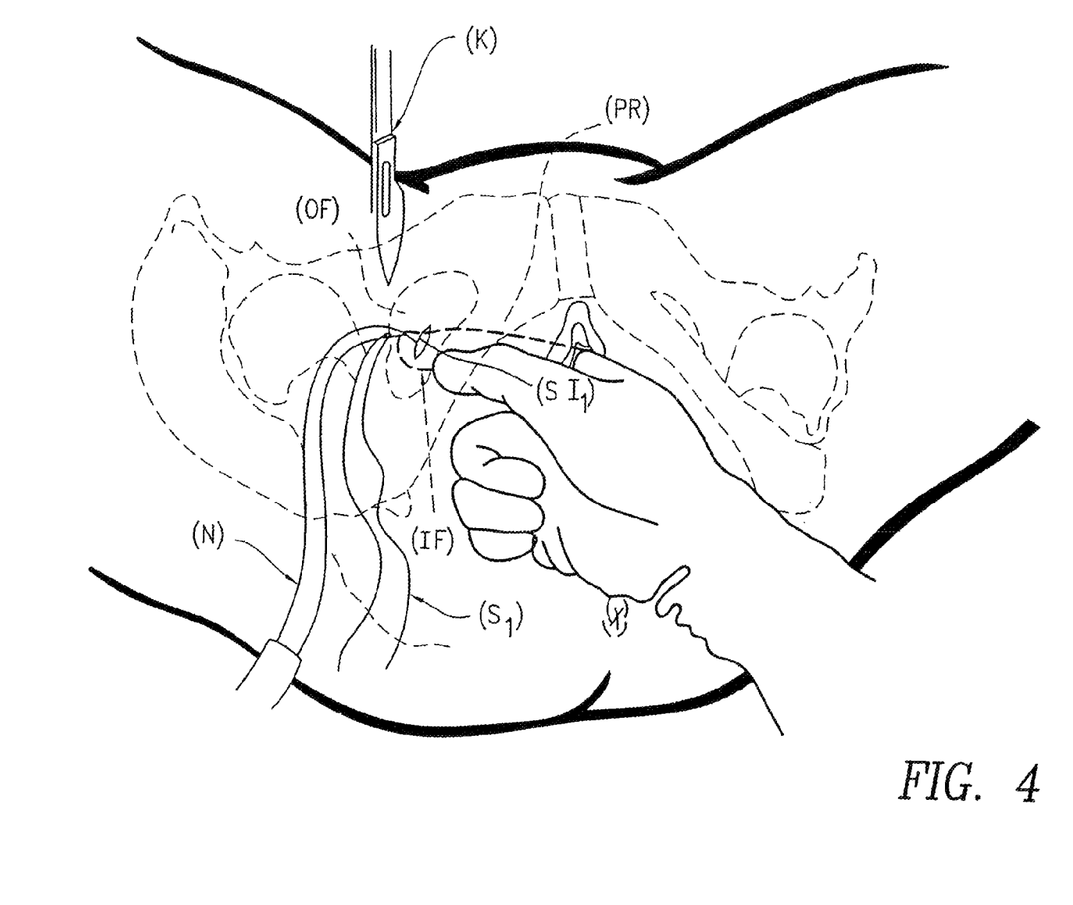
FIGS. 4 and 5 illustrate two stages of a trans-obturator passage which is being performed as part of the surgical procedures depicted in FIG. 3.
Figure 5:
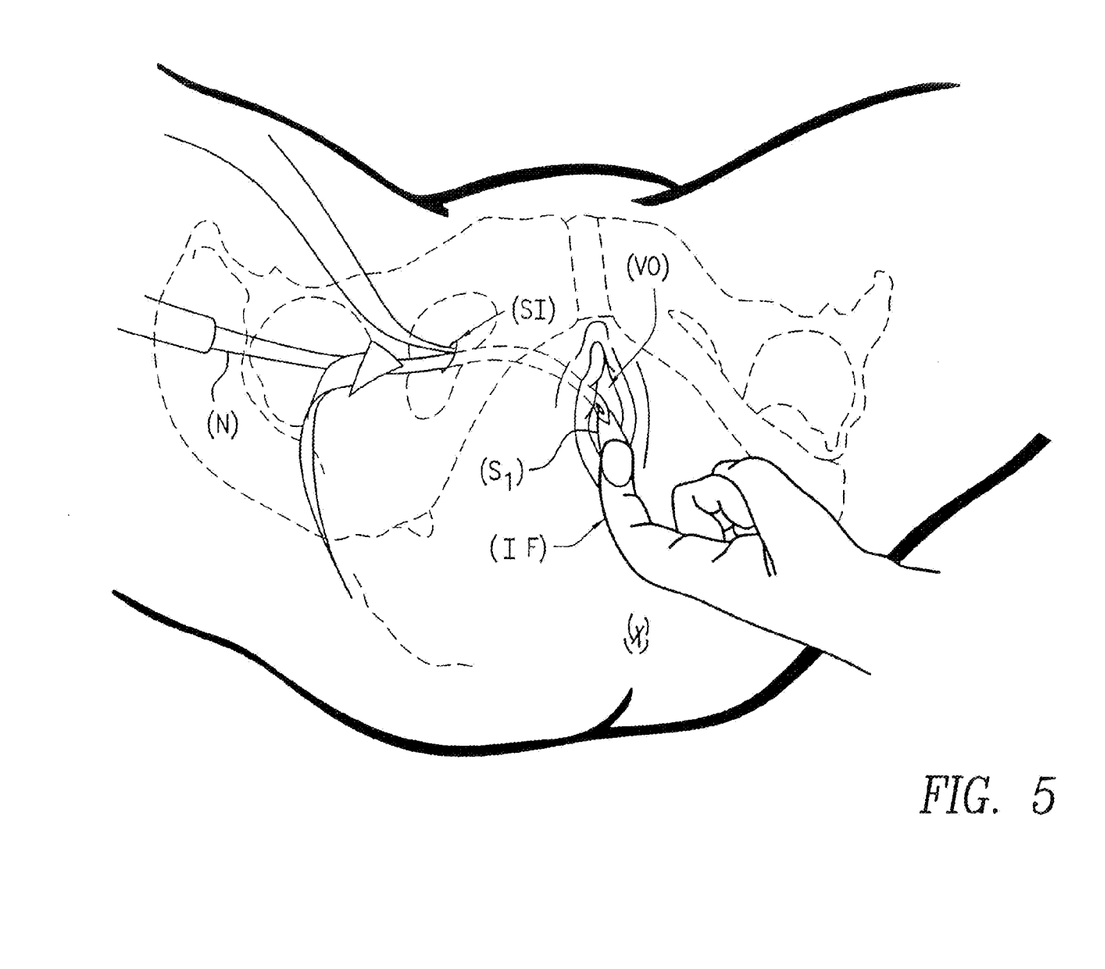

This procedure is illustrated in FIGS. 4 and 5. The ideal zone for such a passage is the inferior and internal part of the obturator foramen, slightly above the ischiopubic ramus (PR). It is located at the level of the arcus tendinosus internally and can be surgically defined by a bi-digital palpation.

Referring to FIG. 4, the surgeon would use a surgical knife (K), such as a scalpel, to make a 5 mm skin incision ($SI_1$), facing the tip of the surgeon's index finger (IF) lateral to the labia majora. A conventional curved and eyed needle (N) adapted to carry a suture ($S_1$) is through the obturator foramen (OF) and then pushed around the ischiopubic ramus (PR) until it comes into contact with the tip of the surgeon's index finger (IF).

With reference now to FIG. 5, the needle (N) is guided by the surgeon's index finger (IF) pushed through the anterior vaginal incision (not shown) until it reaches the vaginal opening (VO). The surgeon can now hook the looped end of the suture ($S_1$) with his or her index finger, pulling it out of the patient through the vaginal opening (VO). After detaching the suture ($S_1$) from the needle (N) and withdrawing the needle (N) back through the skin incision ($SI_1$), the suture ($S_1$) lies freely in the trans-obturator passage ready for attachment to the anterior implant 10 of FIG. 1 as will be described hereinafter.

The same procedure would then be performed on the opposite side of the patient using the same needle (N) or another identical needle. The result would be that there are now two sutures ($S_1$) and ($S_2$) extending from two skin incisions ($SI_1$) and ($SI_2$) to the vaginal opening (VO), where they are ready for attachment to the anterior implant 10 (see FIG. 6).

E. Anterior Implant Fixation

Figure 6:
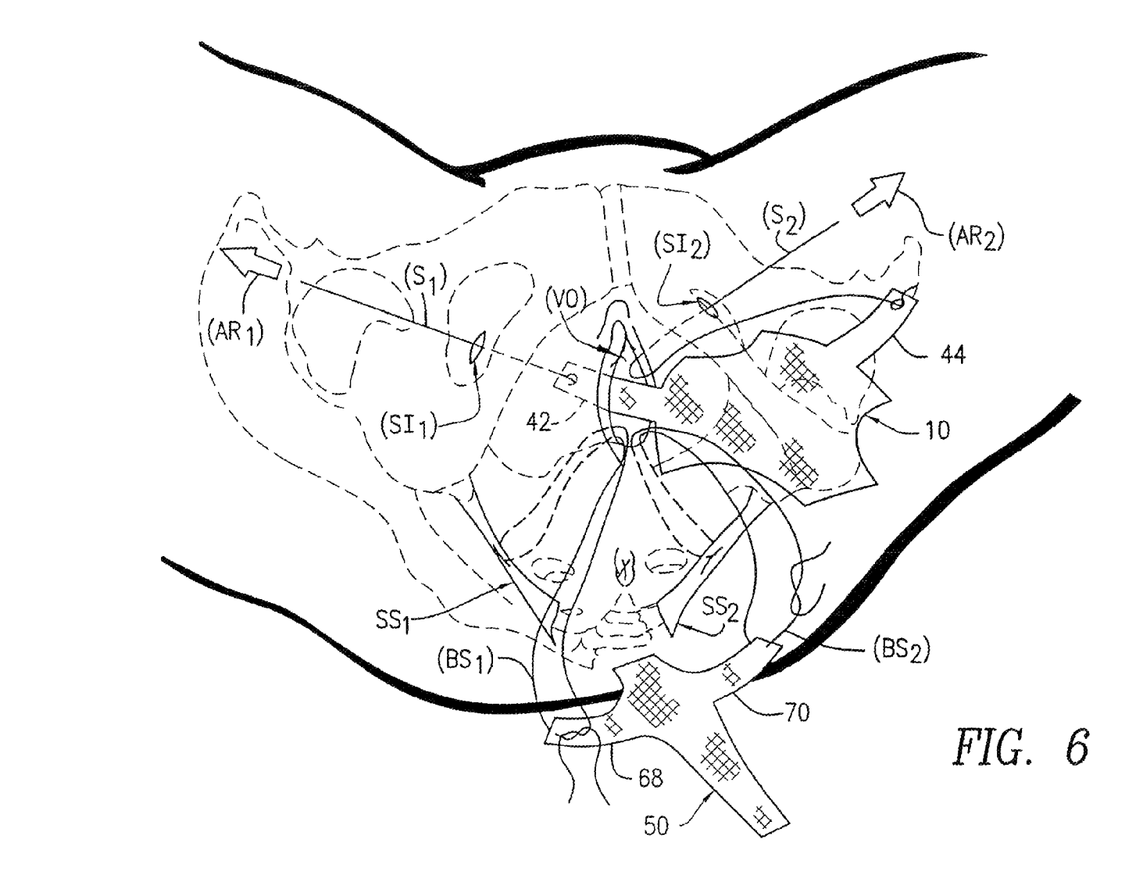
FIG. 6 shows the implants of FIGS. 1 and 2 as they are being implanted in a female patient.

With particular reference to FIG. 6, the two sutures ($S_1$) and ($S_2$) are shown attached to the straps 42, 44, respectively, of the anterior implant 10. As illustrated in FIG. 6, both of the sutures ($S_1$) and ($S_2$) are pulled on in the direction of arrows $AR_1$, and $AR_2$, respectively, while the surgeon inserts the anterior implant 10 into the patient through the vaginal opening (VO) and then through the anterior vaginal incision (not shown). As the sutures ($S_1$) and ($S_2$) are continued to be withdrawn back through the skin incisions ($SI_1$) and ($SI_2$), respectively, the straps 42, 44 pass through their respective obturator membranes, finally emerging through the skin incisions (SI$_1$) and (SI$_2$), respectively. Each of the straps 42, 44 is given the correct tension so that the anterior implant 10 conforms as much as possible to the patient's surrounding tissues. The straps 42, 44 are then cut at skin level and abandoned without any additional fixation. The anterior implant 10 would now be laterally fixated between the bladder (B) and the vagina (V) as shown in FIG. 3. When the endopelvic fascia is strong, the straps 42, 44 can be severed from the anterior implant 10, thereby avoiding the trans-obturator passage. In such a situation, the anterior implant 10 would be fixed laterally by two stitches on each of its sides.

Figure 7:
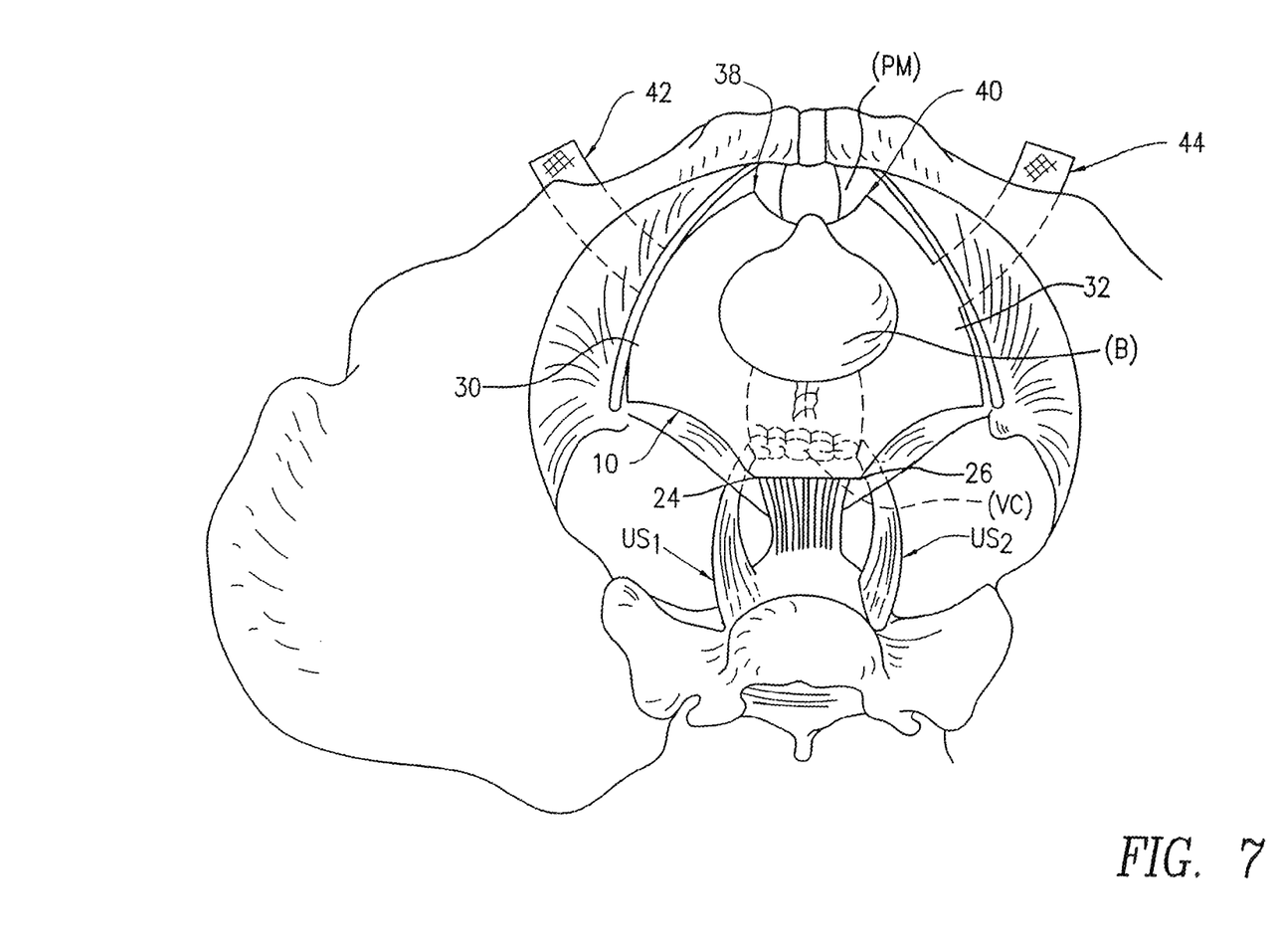
FIG. 7 shows the anterior implant of FIG. 1 in place between a female patient's bladder and vagina.

Referring now to FIG. 7, as well as to FIG. 3, the anterior implant 10 is fixed bilaterally, in the vicinity of the corners 38, 40, to the anterior part of the pubo-coccygeous muscle (PM) close to its insertion by one stitch of braided absorbable size 0 suture, thereby achieving an anterior fixation of the implant. The anterior implant 10 is also fixed bilaterally, in the vicinity of the corners 24, 26, to the utero-sacral ligaments (US$_1$) and (US$_2$) a distance of 1 to 2 cm from the vaginal cuff (VC) by one stitch of braided absorbable size 0 suture. Alternatively, such posterior fixation of the anterior implant 10 can be achieved by attachment to the sacro-spinous ligaments (SS$_1$) and (SS$_2$) bilaterally or to the posterior implant 50, if a posterior repair is to be performed.

If no posterior repair is to be undertaken, an economical colpectomy, which would be limited to the edges of the vaginal incision, is performed as required. The anterior vaginal incision is then closed (as shown in FIGS. 3 and 7) by a continuous absorbable size 0 suture up to the vaginal apex, making sure that the vaginal wall is not under tension.

With continuing reference to FIGS. 3 and 7, a person skilled in the art will readily appreciate that the anterior implant 10 functions to repair lateral cystoceles, as well as a medial or central cystocele. It should also be understood that the straps 42, 44 of the anterior implant 10 provide adequate lateral fixation so as to eliminate the need to stitch or staple the convex side edges 30, 32 to the arcus tendineous fascia pelvis (ATFP), thereby avoiding a very difficult and time-consuming stitching or stapling procedure.

III. Posterior Repair

A. Incision of the Perineum

This procedure, which is well known in the art and which is not depicted in the accompanying drawings, involves two basic steps. These steps are as follows: (1) the triangular incision of the perineal skin and excision; and (2) dissection of the perineal body.

B. Incision of the Posterior Vaginal Wall

The full thickness of the posterior vaginal wall is incised longitudinally from the perineal incision either up to 2 cm from the vaginal apex or up to the vaginal apex, thereby creating an appropriately sized posterior vaginal incision. While this procedure is not illustrated in the accompanying drawings, it is well known in the art.

C. Rectal Dissection

The anterior and lateral wall of the rectum is bluntly dissected from the vagina.

Since this procedure is well known to a person skilled in the art, it has not been depicted in the accompanying drawings     D. Para-Rectal Space Dissection     Initially, the para-rectal space is entered bilaterally by gentle dissection. It is then dissected more deeply until the sacro-spinuous ligaments are exposed or simply palpated. Again, while this procedure is not illustrated in the accompanying drawings, it is well known in the art.

E. Plication of the Pre-Rectal Fascia

This procedure is typically performed using a continuous suture of 2/0 absorbable monofilament suture. Because this procedure is well known in the art, it too has not been depicted in the accompanying drawings.

F. Posterior Implant Fixation

With reference to FIG. 6, lateral fixation of the posterior implant 50 of FIG. 2 is achieved by inserting non-absorbable size 0 braided sutures (BS$_1$) and (BS$_2$) into the sacro-spinous ligaments (SS$_1$) and (SS$_2$), respectively, 2 to 3 cm medial to the sciatic spine on both sides of the patient's body. After attaching the straps 68, 70 of the posterior implant 50 to the braided sutures (BS$_1$) and (BS$_2$), respectively, the implant is inserted into the patient's body through the vaginal opening (VO) and then through the posterior vaginal incision (not shown). The braided sutures (BS$_1$) and (BS$_2$) are then used to attach their associated straps 68, 70 to the sacro-spinous ligaments (SS$_1$) and (SS$_2$), respectively, such that the posterior implant 50 is positioned between the vagina (V) and the rectum (R) as illustrated best in FIG. 8. It is also possible to attach the straps 68, 70 to the sacro-spinous ligaments (SS$_1$) and (SS$_2$) using glue, staples, tacks, anchors (e.g., MITEK's "Fastin" threaded anchor or INFLUENCE's "Raz" soft-tissue anchoring system) or sewing devices such as United States Surgical Corporation's "Endostitch" mechanism.

Figure 8:
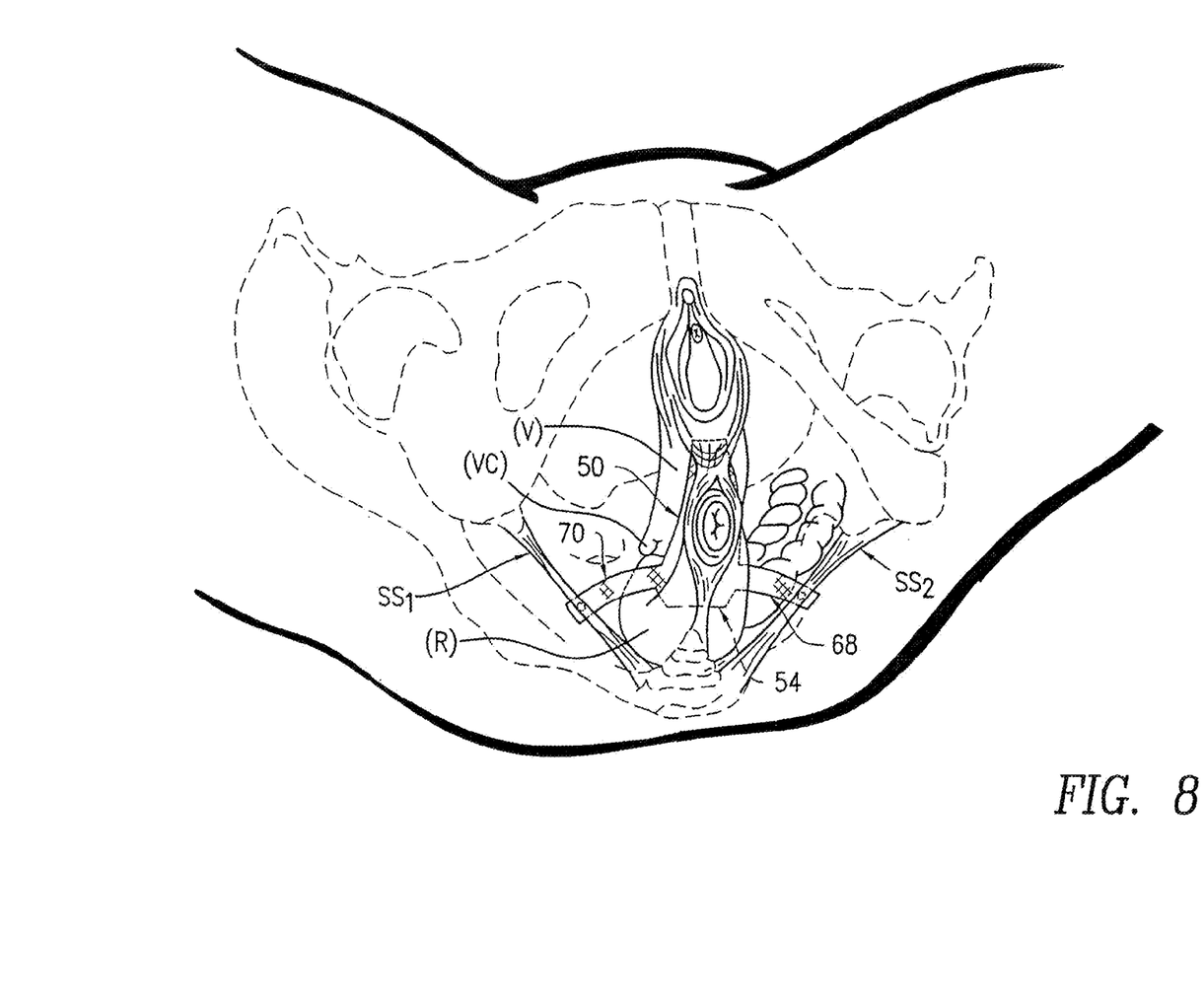
FIGS. 8 and 9 show the posterior implant of FIG. 2 in place between a female patient's rectum and vagina.

Referring now to FIG. 8, as well as to FIG. 3, upper fixation of the posterior implant 50 is achieved by applying the upper portion 54 to the anterior wall of the high rectum without any fixation. Alternatively, and with reference to FIG. 3, the upper portion 54 of the posterior implant 50 can be fixed to the utero-sacral ligaments (US$_1$) and (US$_2$) by stitching or any other suitable means known in the art; or, if an anterior repair has been performed, it can be folded over the vaginal cuff (VC) and then attached to the lower portion 12 of the anterior implant to between the corners 24, 26 thereof.

Figure 9:
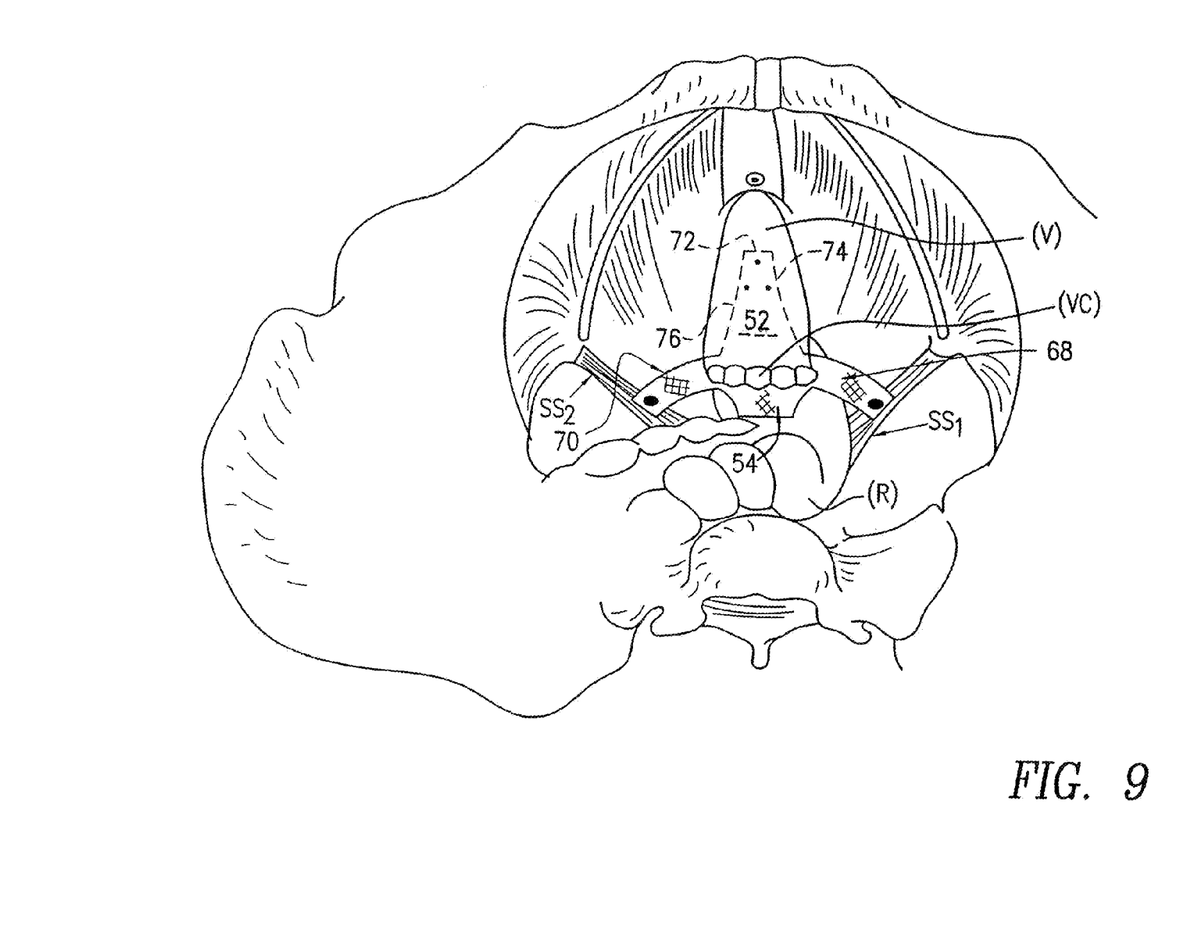

With continuing reference to FIGS. 3, 8 and 9, lower fixation of the posterior implant 50 is achieved by applying the lower portion 52 of the implant to the anterior wall of the mid and low rectum. The edges 74, 76 of the lower portion 52 are fixed to the pubo-rectal muscle by one or two stitches of absorbable braided 2/0 sutures (see FIGS. 3 and 8). The lower edge 72 (i.e., the free end) of the lower portion 52 is attached to the perineal body (see FIG. 9) in order to treat or prevent associated descending perineum.

With the posterior implant 50 properly positioned between the vagina (V) and the rectum (R), the posterior repair is now complete. Closure of the posterior vaginal incision (not shown) is typically achieved by a continuous absorbable size 0 suture starting at the vaginal apex, making sure that the posterior vaginal wall is not under tension. A standard perineorraphy is then performed covering the distal part of the posterior implant 50.

IV. Apical Repair

Apical fixation can be performed in accordance with three different techniques. Each of these techniques will be described below.

In accordance with one technique, the vaginal vault is fixed by the attachment between the utero-sacral ligaments and the anterior implant 10 and/or the posterior implant 50 (see FIG. 3). The suture is applied transversely, if the utero-sacral ligaments remain distinct, or longitudinally, if such ligament have been brought together as per the McCall type culdeplasty.

Another technique involves attaching the vaginal vault to the anterior implant 10 and/or the posterior implant 50 by trans-fixating absorbable 2/0 braided sutures. Like the preceding technique, this technique uses one or both of the implants 10, 50 to achieve the desired apical fixation.

The other apical fixation technique does not make direct use of either the anterior implant 10 or the posterior implant 50. More particularly, the vaginal vault is fixed independently of either of the implants 10, 50 by a standard bilateral sacrospinous fixation.

Figure 10:
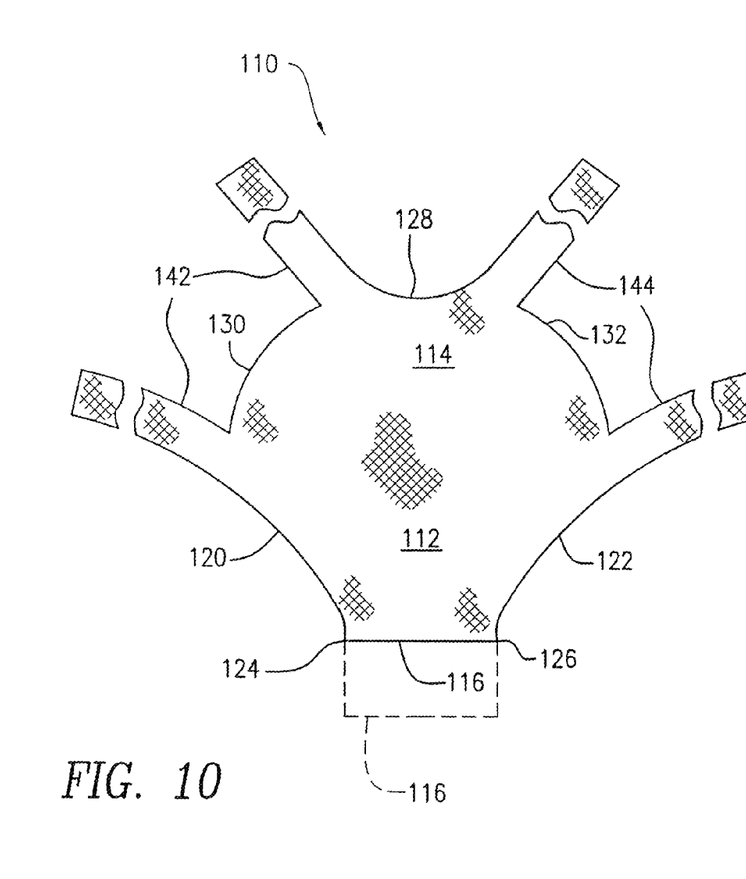
FIG. 10 is a top plan view of another exemplary embodiment of an anterior implant constructed in accordance with the present invention.
Figure 11:
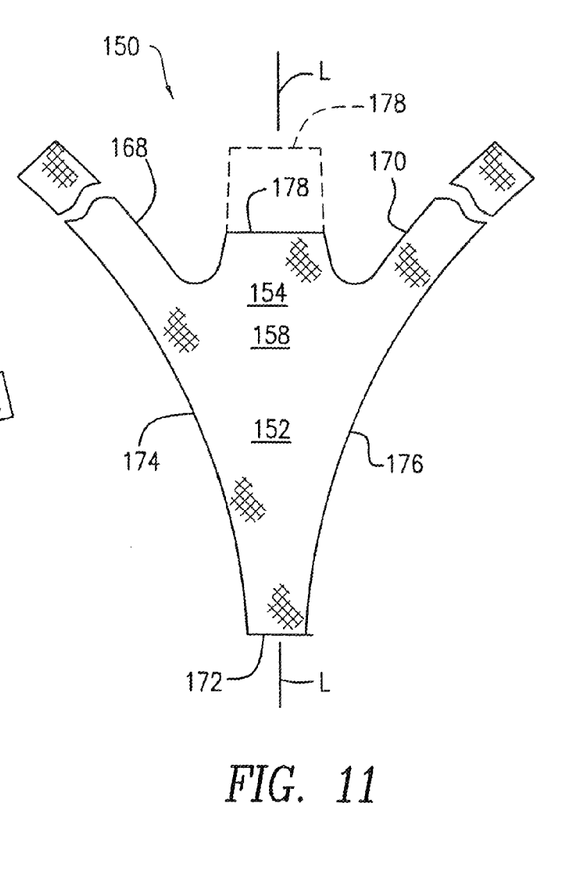
FIG. 11 is a top plan view of another exemplary embodiment of a posterior implant constructed in accordance with the present invention.

What follows is a description of the two alternate embodiments referred to above and illustrated in FIGS. 10 and 11. In describing these alternate embodiments, elements which correspond to elements described above in connection with the embodiments of FIGS. 1 and 2 will be designated by corresponding reference numerals increased by one hundred. Unless otherwise specified, the alternate embodiments of FIGS. 10 and 11 are constructed and operate in the same manner as the embodiments of FIGS. 1 and 2, respectively.

Referring to FIG. 10, there is shown an anterior implant 110 whose main difference in comparison to the anterior implant 10 of FIG. 1 involves the provision of two straps 142 on one side of the anterior implant 110 and two straps 144 on the opposite side of the anterior plant 110. Both of the straps 142 pass through the obturator foramen on one side of a patient, while both of the straps 144 pass through the obturator foramen on the other side of the patient's body. Each of the straps 142 exits the patient's body through a corresponding one of two small skin incisions at the perineum (i.e., groin) on one side of the body. Similarly, each of the straps 144 exits the patient's body through a corresponding one of two small skin incisions at the perineum (i.e., groin) on the other side of the body. As compared with the anterior implant 10, the anterior implant 110 provides increased lateral support in use as a result of the provision of the extra set of straps 142, 144, whose location allows the anterior implant 110 to be manufactured without the corners 34, 36 and 38, 40 which are characteristic of the anterior implant 10.

With reference to FIG. 11, there is shown a posterior implant 150 whose main difference in comparison to the posterior implant 50 of FIG. 2 involves the acute angle that straps 168, 170 form with the central longitudinal axis (L) of the anterior implant 150. The angle is specifically selected so asp to reduce the amount of rectal constriction in the event that the posterior implant 150 shrinks when implanted in a patient's body.

It should be understood that the various embodiments described herein are merely exemplary and that a person skilled in the art may make many variations and modifications without departing from the spirit and scope of the invention as defined in the appended claims. For instance, if the uterus is conserved (i.e., no hysterectomy), the posterior fixation of the anterior implant 10 is done on the anterior part of the cervix, with the upper portion 54 of the posterior implant 50 being fixed on the posterior part of the cervix. Also, once the-prolapse repair has been completed in accordance with the present invention, a vaginal incision can be made at the mid-urethral level and a sub-urethral sling inserted in accordance with a well known treatment for stress urinary incontinence. These and any and all additional variations and modifications are intended to be included within the scope of the invention as defined in the appended claims.

The invention claimed is:

1. A procedure for treating pelvic organ prolapse in a female patient, comprising the steps of:
    via a vaginal incision, placing an implant between the patient's rectum and vagina to perform a posterior repair, wherein said implant has a main body portion and at least first and second straps extending outwardly from said main body portion;
    attaching said first strap to one of the patient's sacrospinous ligaments; and
    attaching said second strap to the other one of the patient's sacrospinous ligaments,
    whereby said main body portion provides support to said prolapsed organ via said attached first and second straps.

2. The procedure according to claim 1, wherein said attaching steps further comprise attaching said first and second straps to the patient's respective sacrospinous ligaments using a soft tissue anchor.

3. A procedure for treating pelvic organ prolapse in a female patient, comprising the steps of:
    utilizing an implant having a main body portion and at least first and second straps extending outwardly from said main body portion;
    attaching said first strap to one of the patient's sacrospinous ligaments;
    attaching said second strap to the other one of the patient's sacrospinous ligaments, and
    positioning said implant between the patient's vagina and rectum so that said main body portion provides support to the prolapsed organ via said first and second straps.

4. The procedure according to claim 3, wherein said attaching steps further comprise attaching said first and second straps to the patient's respective sacrospinous ligaments using a soft tissue anchor.

* * * * *